United States Patent
Pratt et al.

(10) Patent No.: US 11,512,262 B2
(45) Date of Patent: Nov. 29, 2022

(54) AZAPHENOTHIAZINES AND AZAPHENOXAZINES AS ANTIOXIDANTS

(71) Applicant: University of Ottawa, Ottawa (CA)

(72) Inventors: Derek Andrew Pratt, Ottawa (CA); Evan Haidasz, Hoboken, NJ (US)

(73) Assignee: University of Ottawa, Ottawa (CA)

( * ) Notice: Subject to any disclaimer, the term of this patent is extended or adjusted under 35 U.S.C. 154(b) by 0 days.

(21) Appl. No.: 16/494,936

(22) PCT Filed: Mar. 15, 2018

(86) PCT No.: PCT/CA2018/050314
§ 371 (c)(1),
(2) Date: Sep. 17, 2019

(87) PCT Pub. No.: WO2018/165760
PCT Pub. Date: Sep. 20, 2018

(65) Prior Publication Data
US 2020/0010776 A1    Jan. 9, 2020

Related U.S. Application Data

(60) Provisional application No. 62/472,812, filed on Mar. 17, 2017.

(51) Int. Cl.
*C10M 169/04* (2006.01)
*C07D 498/04* (2006.01)
(Continued)

(52) U.S. Cl.
CPC ......... *C10M 169/04* (2013.01); *C07D 498/04* (2013.01); *C07D 513/04* (2013.01); *C07D 513/14* (2013.01); *C10M 133/48* (2013.01);

*C10M 135/36* (2013.01); *C10M 2203/003* (2013.01); *C10M 2215/30* (2013.01);
(Continued)

(58) Field of Classification Search
CPC .. C07D 498/04; C07D 513/04; C07D 513/14; C10M 169/04; C10M 133/48; C10M 135/36; C10M 2203/003; C10M 2215/30; C10M 2219/104; C10N 2040/25; C10N 2030/10
See application file for complete search history.

(56) References Cited

U.S. PATENT DOCUMENTS 2,813,828 A    11/1957  Woods
3,118,884 A    1/1964   Clarke
(Continued)

FOREIGN PATENT DOCUMENTS

CA    2187946 A1    11/1995
CN    104311508 A    1/2015
(Continued)

OTHER PUBLICATIONS

CAS RN: 109602-14-4; STN entry date: Aug. 1, 1987; picrate|OH-Pyrido[3,2-b][1,4]benzothiazine (1 Page).
(Continued)

*Primary Examiner* — Vishal V Vasisth
(74) *Attorney, Agent, or Firm* — Clark & Elbing LLP

(57) ABSTRACT

The present disclosure relates generally to antioxidants. More particularly, the present disclosure relates to lubricating compositions comprising an antioxidant.

21 Claims, 3 Drawing Sheets

Hexadecane Autoxidations at 160°C

Hydroperoxide formation in n-hexadecane autoxidations at 160°C, uninhibited (black), and inhibited with 100µM of DTA (red), 1 (purple), 2 (blue), 3 (brown), and 4 (gold).

(51) Int. Cl.

| | |
|---|---|
| C07D 513/04 | (2006.01) |
| C07D 513/14 | (2006.01) |
| C10M 133/48 | (2006.01) |
| C10M 135/36 | (2006.01) |
| C10N 30/10 | (2006.01) |
| C10N 40/25 | (2006.01) |

(52) U.S. Cl.
CPC ... C10M 2219/104 (2013.01); C10N 2030/10 (2013.01); C10N 2040/25 (2013.01)

(56) References Cited

U.S. PATENT DOCUMENTS

| | | | | |
|---|---|---|---|---|
| 5,026,846 | A * | 6/1991 | Duchesne | C07D 513/04 544/1 |
| 5,446,148 | A | 8/1995 | Kutscher et al. | |
| 5,614,124 | A * | 3/1997 | Esche, Jr. | C10M 163/00 508/251 |
| 7,176,168 | B2 | 2/2007 | Vann et al. | |
| 2007/0203033 | A1 | 8/2007 | Tynik et al. | |
| 2010/0285087 | A1 | 11/2010 | McDonough et al. | |
| 2011/0030269 | A1 * | 2/2011 | Chasan | C10M 133/12 44/388 |
| 2018/0265800 | A1 * | 9/2018 | Rabbat | C07D 513/04 |

FOREIGN PATENT DOCUMENTS

| | | |
|---|---|---|
| DE | 1110651 B | 7/1961 |
| EP | 3279296 A1 | 2/2018 |
| FR | 2643266 A1 | 8/1990 |
| GB | 990857 A | 5/1965 |
| JP | 39000493 | 1/1964 |
| KR | 10-2015-0012906 A | 2/2015 |
| WO | WO-95/31522 A1 | 11/1995 |
| WO | WO-99/13038 A1 | 3/1999 |
| WO | WO-2016/158615 A1 | 6/2016 |
| WO | WO-2017/040965 A1 | 9/2017 |

OTHER PUBLICATIONS

CAS RN: 112723-37-2; STN entry date: Feb. 6, 1988; 8-(trifluoromethyl)-10H-Pyrido[3,2-b][1,4]benzothiazine (1 Page).

CAS RN: 117000-77-8; STN entry date: Oct. 22, 1988; 8-(methylthio)-10H-Pyrido[3,2-b][1,4]benzothiazine (1 Page).

CAS RN: 118401-99-3; STN entry date: Jan. 13, 1989; 1 H-Pyrido[3,2-b][1,4]benzothiazinol (1 Page).

CAS RN: 1207-97-2; STN entry date: Nov. 16, 1984; 10H-Pyrimido[5,4-b][1,4]benzothiazin-2-amine (1 Page).

CAS RN: 1207-98-3; STN entry date: Nov. 16, 1984; 1H-Pyrimido[5,4-b][1,4]benzothiazin-2(3H)-one (1 Page).

CAS RN: 121697-82-3; STN entry date: Jul. 21, 1989; 1H-Pyrido[3,2-b][1,4]benzothiazine-2,3,7,9-d4 (1 Page).

CAS RN: 121714-87-2; STN entry date: Jul. 21, 1989; 1H-Pyrido[3,2-b][1,4]benzothiazine, labeled with deuterium (1 Page).

CAS RN: 1370030-92-4; STN entry date: Apr. 19, 2012; 8-(trifluoromethyl)-10H-Pyrido[3,2-b][1,4]benzoxazine (1 Page).

CAS RN: 1402737-48-7; STN entry date: Nov. 1, 2012; 2-[(trimethylsilyl)oxy]-(CAINDEXNAME)l0H-Pyrimido[5,4-b][1,4]benzothiazine (1 Page).

CAS RN: 1434143-73-3; STN entry date: Jun. 4, 2013; 1H-Pyrimido[ 5,4-b][1,4]benzoxazine-2(3H)-thione (1 Page).

CAS RN: 1579296-08-4; STN entry date: Apr. 2, 2014; 8-methoxy-1H-Pyrimido[ 5,4-b][1,4]benzothiazin-2(3H)-one (1 Page).

CAS RN: 158438-82-5; STN entry date: Oct. 20, 1994; hydrochloride(1:1) 8-(trifluoromethyl)-10H-Pyrido[3,2-b][1,4]benzothiazine (1 Page).

CAS RN: 158438-83-6; STN entry date: Oct. 20, 1994; 2-methyl-10H-Pyrido[3,2-b][1,4]benzothiazine (1 Page).

CAS RN: 158438-86-6; STN entry date: Oct. 20, 1994; hydrochloride (1:1) 10H-Pyrido[3,2-b][1,4]benzothiazine (1 Page).

CAS RN: 161876-96-6; STN entry date: Mar. 31, 1995; 1H-Pyrimido[5,4-b][1,4]benzoxazine (1 Page).

CAS RN: 1684-72-6; STN entry date: Nov. 16, 1984; 2-(4-methyl-1-piperazinyl)-(CAINDEXNAME)OTHER10H-Pyrimido[5,4-b][1,4]benzothiazine (1 Page).

CAS RN: 1684-73-7; STN entry date: Nov. 16, 1984; 2-(4-morpholinyl)-10H-Pyrimido[5,4b][1,4]benzothiazine (1 Page).

CAS RN: 1684-74-8; STN entry date: Nov. 16, 1984; 2-(1-piperidinyl)-10H-Pyrimido[5,4b][1,4]benzothiazine (1 Page).

CAS RN: 1684-78-2; STN entry date: Nov. 16, 1984; 2-(2-methoxyethoxy)-(CAINDEXNAME)OTHER10H-Pyrimido[5,4-b][1,4]benzothiazine (1 Page).

CAS RN: 1684-80-6; STN entry date: Nov. 16, 1984; N1,N1-dimethyl-N2-10H-pyrimido[5,4b][1,4]benzothiazin-2-yl-1,2-Ethanediamine (1 Page).

CAS RN: 1811-90-1; STN entry date: Nov. 16, 1984; 1H-Pyrimido[5,4b][1,4]benzothiazine2(3H)thione (1 Page).

CAS RN: 1811-91-2; STN entry date: Nov. 16, 1984; N1,N1-dimethyl-N3-10H-pyrimido[5,4b][1,4]benzothiazin-2-yl-1,3-Propanediamine (1 Page).

CAS RN: 1844-35-5; STN entry date: Nov. 16, 1984; 1H-Pyrimido[5,4-b][1,4]benzothiazin-2(3H)-one, sodium salt (1:1) (CAINDEXNAME)OTHER (1 Page).

CAS RN: 1844-36-6; STN entry date: Nov. 16, 1984; 2-methoxy-10H-Pyrimido[5,4b][1,4]benzothiazine (1 Page).

CAS RN: 203647-97-6; STN entry date: Apr. 5, 1998; 1-(5H-pyrido[3,4-b][l,4]benzothiazin-7-ylmethyl)-(CAINDEXNAME)4(1H)-Pyridinone (1 Page).

CAS RN: 203648-23-1; STN entry date: Apr. 5, 1998; 7-(1-piperidinylmethyl)-(CAINDEXNAME)5H-Pyrido[3,4-b][1,4]benzothiazine (1 Page).

CAS RN: 203648-34-4; STN entry date: Apr. 5, 1998; N,N-dimethyl-N'-[1-(5H-pyrido[3,4-b][1,4]benzothiazin-7-ylmethyl)-4-piperidinyl]-Sulfamide (1 Page).

CAS RN: 203648-46-8; STN entry date: Apr. 5, 1998; N,N-dimethyl-N'-[1-(10H-pyrimido[5,4-b][1,4]benzothiazin-8-ylmethyl)-4-piperidinyl]-Sulfamide (1 Page).

CAS RN: 203648-52-6; STN entry date: Apr. 5, 1998; N-methyl-N'-[1-(10H-pyrido[3,2-b][1,4]benzothiazin-8-ylmethyl)-4-piperidinyl]-Sulfamide (1 Page).

CAS RN: 203649-98-3; STN entry date: Apr. 5, 1998; ethyl estera-methyl-1-(10H-pyrido[3,2-b][1,4]benzothiazin-8-ylmethyl)-4-Piperidinepentanoic acid (1 Page).

CAS RN: 203650-36-6; STN entry date: Apr. 5, 1998; a-methyl-1-(10H-pyrido[3,2-b][1,4]benzothiazin-8-ylmethyl)-4-Piperidinebutanoic acid (1 Page).

CAS RN: 203650-38-8; STN entry date: Apr. 5, 1998; a-methyl-1-(10H-pyrimido[5,4-b][1,4]benzothiazin-8-ylmethyl)-4-Piperidinebutanoic acid (1 Page).

CAS RN: 203650-44-6; STN entry date: Apr. 5, 1998; a-methyl-1-(10H-pyrido[3,2-b][1,4]benzothiazin-8-ylmethyl)-4-Piperidinepentanoic acid (1 Page).

CAS RN: 203650-61-7; STN entry date: Apr. 5, 1998; a-methyl-1-(5H-pyrido[3,4-b][1,4]benzothiazin-7-ylmethyl)-4-Piperidinebutanoic acid (1 Page).

CAS RN: 203659-35-2; STN entry date: Apr. 5, 1998; 5H-Pyrido[3,4-b][1,4]benzothiazine-7-acetonitrile (1 Page).

CAS RN: 203659-36-3; STN entry date: Apr. 5, 1998; 5H-Pyrido[3,4-b][1,4]benzothiazine-7-ethanimidamide, N-cyano-,hydrochloride (1:2) (1 Page).

CAS RN: 203659-37-4; STN entry date: Apr. 5, 1998; a-4-morpholinyl-5H-Pyrido[3,4-b][1,4]benzothiazine-7-ethanimine (1 Page).

CAS RN: 203659-38-5; STN entry date: Apr. 5, 1998; (2S)-1-[1-imino-2-(5H-pyrido[3,4-b][1,4]benzothiazin-7-yl)ethyl]-2-Pyrrolidinecarboxamide (1 Page).

CAS RN: 203661-40-9; STN entry date: Apr. 5, 1998; 10H-Pyrimido[5,4-b][1,4]benzothiazine-8-methanol (1 Page).

CAS RN: 203661-45-4; STN entry date: Apr. 5, 1998; 10H-Pyrido[3,2-b][1,4]benzothiazine-8-methanol (1 Page).

CAS RN: 203661-49-8; STN entry date: Apr. 5, 1998; 8-(chloromethyl)-10H-Pyrido[3,2-b][1,4]benzothiazine (1 Page).

(56) References Cited

OTHER PUBLICATIONS

CAS RN: 2083630-53-7; STN entry date: Mar. 9, 2017; 8-(diethylamino)-(CAINDEXNAME)1H-Pyrimido[5,4-b][1,4]benzothiazin-2(3H)-one (1 Page).
CAS RN: 2089388-24-7; STN entry date: Apr. 11, 2017; Index name not yet assigned (1 Page).
CAS RN: 2089388-28-1; STN entry date: Apr. 11, 2017; N,N-diethyl-10H-Pyriraido[5,4-b][1,4]benzoxazin-2-amine (1 Page).
CAS RN: 2167630-27-3; STN entry date: Jan. 1, 2018; 2H-Pyrido[3,4-b][1,4]benzothiazin-3(5H)-one (1 Page).
CAS RN: 2318-58-3; STN entry date: Nov. 16, 1984; 2-hydrazinyl-10H-Pyrimido[5,4b][1,4]benzothiazine (1 Page).
CAS RN: 2469-30-9; STN entry date: Nov. 16, 1984; hydrochloride (1:1) (CAINDEXNAME)OTHER10H-Pyrimido[5,4-b][1,4]benzothiazin-2-amine (1 Page).
CAS RN: 261-80-3; STN entry date: Nov. 16, 1984; 5H-Pyrido[3,4-b][1,4]benzoxazine (1 Page).
CAS RN: 261-83-6; STN entry date: Nov. 16, 1984; 10H-Pyrido[3,2-b][1,4]benzoxazine (1 Page).
CAS RN: 261-90-5; STN entry date: Nov. 16, 1984; 5H-Pyrido[3,4-b][1,4]benzothiazine (1 Page).
CAS RN: 261-96-1; STN entry date: Nov. 16, 1984; 10H-Pyrido[3,2-b][1,4]benzothiazine (1 Page).
CAS RN: 261-98-3; STN entry date: Nov. 16, 1984; 10H-Pyrimido[5,4-b][1,4]benzothiazine (1 Page).
CAS RN: 262-01-1; STN entry date: Nov. 16, 1984; 5H-Dipyrido[3,4-b:4',3'-e][1,4]thiazine (1 Page).
CAS RN: 67443-26-9; STN entry date: Dec. 18, 1984; 8-methyl-10H-Pyrido[3,2-b][1,4]benzoxazine (1 Page).
CAS RN: 748752-30-9; STN entry date: Sep. 21, 2004; N-cyano-(CAINDEXNAME)5H-Pyrido[3,4-b][1,4]benzothiazine-7-ethanimidamide (1 Page).
CAS RN: 857199-41-8; STN entry date: Jul. 7, 2005; 10H-Pyrido[3,2-b][1,4]benzothiazine-8-thiol (1 Page).
CAS RN: 94785-81-6; STN entry date: Feb. 17, 1985; 2-methyl-10H-Pyrimido[5,4-b][1,4]benzothiazine (1 Page).
CAS RN: 95047-47-5; STN entry date: Mar. 3, 1985; hydrochloride (1:?) 5H-Pyrido[3,4-b][1,4]benzoxazine (1 Page).
CAS RN: 957997-21-6; STN entry date: Dec. 14, 2007; 1H-Pyrimido[5,4-b][1,4]benzoxazin-2(3H)-one (1 Page).
Extended European Search Report for European Patent Application No. 18767504.6, dated Dec. 9, 2020.
Haidasz, E. et al., "Diazaphenoxazines and Diazaphenothiazines: Synthesis of the "Correct" Isomers Reveals They Are Highly Reactive Radical-Trapping Antioxidants," Org. Lett. 19(7):1854-1857 (2017).
Hu and Zhang., "Method for the Synthesis of Phenothiazines via a Domino Iron-catalyzed C-S/C-N Cross-coupling Reaction," The Journal of Organic Chemistry. 80(12):6128-6132 (2015).
International Preliminary Report on Patentability for International Patent Application No. PCT/CA2018/050314, dated Sep. 17, 2019.
International Search Report and Written Opinion for International Application No. PCT/CA2018/050314 dated Jun. 15, 2018 (17 pages).
Ito et al., "Syntheses of Nitrogen-Containing Heterocyclic Compounds XXIX—An Improved Method for the Preparation of 10h-pyrido [3, 2-b]-[1, 4] Benzoxazine (1-azaphenoxazine)," Chemical and Pharmaceutical Bulletin. 26(5):1375-1383 (1978).
Kushwaha et al., "Novel Aminoalkylated Azaphenothiazines as Potential Inhibitors of T98G, H460 and Snu80 Cancer Cell Lines in Vitro," Bioorganic and Medicinal Chemistry Letters. 26(9):2237-2244 (2016).
Madrid et al., "Synthesis and Antitubercular Activity of Phenothiazines With Reduced Binding to Dopamine and Serotonin Receptors," Bioorganic and Medicinal Chemistry Letters. 17(11):3014-3017(2007).
Morak-Mlodawska et al., "Synthesis, Spectroscopic Characterization, and Anticancer Activity of New 10-substituted 1,6-diazaphenothiazines," Medicinal Chemistry Research. 25(11):2425-2433 (2016).
Rodig et al., "Pyridine Chemistry. II. Further Studies on the Smiles Rearrangement of the 3-amino-,2, 2'-dipyridyl Sulfide System. The Synthesis of Some 1,6-Diazaphenothiazines," Journal of Medicinal Chemistry. 9(1):116-120 (1966).
Roth and Chloemer., "5-Arylthiopyrimidines. III. Cyclization of 4-Hydroxy Derivatives to 10H-Pyrimido[5,4-b][1,4]benzothiazines (1,3-Diazaphenothiazines)1," The Journal of Organic Chemistry. 28(10):2659-2672 (1963).
Shen and Wu., "Base-Regulated Tunable Synthesis of Pyridobenzoxazepinones and Pyridobenzoxazines," Catalysis Science & Technology. 5(9):4433-4443 (2015).
Takahashi and Maki., "Sulfur-Containing Pyridine Derivatives. LVI. Smiles Rearrangement of Pyridine Derivatives and Synthesis of Benzopyrido- and Dipyrido-1, 4-thiazine Derivatives. 4," Chemical and Pharmaceutical Bulletin. 6(4):369-373 (1958).
Takahashi and Yoneda., "Synthesis of Heterocyclic Compounds With Nitrogen CXIII. Synthesis of Azaphenoxazine Derivatives. 2," Chem Pharm Bull (Tokyo). 6(4):378-381 (1958) (Article in German).
Thome and Bolm., "Transition-Metal-Free Intramolecular N-Arylations," Org Lett. 14(7):1892-1895 (2012).
Hanthorn et al., "The Reactivity of Air-Stable Pyridine- and Pyrimidine-Containing Diarylamine Antioxidants," J Org Chem. 77:6895-6907 (2012).
Maki, "Sulfur-containing Pyridine Derivatives. LIII. Smiles Rearrangement in Pyridine Derivatives and Synthesis of Azaphenothiazine Derivatives. (1).," Pharmaceutical Institute, Medical Faculty, University of Kyoto. 77(5):485-90 (1957).
Shah et al., "Unprecedented Inhibition of Hydrocarbon Autoxidation by Diarylamine Radical-Trapping Antioxidants," J Am Chem Soc. 137:2440-2443 (2015).
Poon et al., "Temperature-dependence of radical-trapping activity of phenoxazine, phenothiazine and their aza-analogues clarifies the way forward for new antioxidant design," Chem Sci. 12(33):11065-11079 (2021) (15 pages).
Bräuniger et al., "10. On the nuclear acylation of 1-methylphenothiazine. 7. On phenothiazine compounds," Archiv der Pharmazie und Berichte der Deutschen Pharmazeutischen Gesellschaft. 298(9):627-34(1965).
Schenker et al., "Phenothiazine and azaphenothiazine," *Progress in Drug Research*, vol. 5. Ernst Jucker, 269-627 (1963) (369 pages).

\* cited by examiner

Hexadecene/PBD-BODIPY Autoxidations at 70° and 100°C

Co-autoxidation of 2.8M hexadecane and 10μM PBD-BODIPY at 70°C in PhCl, initiated by 87mM $^tBu_2O_2$ (black, no inhibitor), and inhibited by 0.6μM 1 (green), 2 (red), or 9 (blue).

Hydroperoxide formation in n-hexadecane autoxidations at 160°C, uninhibited (black), and inhibited with 100μM of DTA (red), 1 (purple), 2 (blue), 3 (brown), and 4 (gold).

Hydroperoxide formation in n-hexadecane autoxidations at 160°C, uninhibited (black), and inhibited with 100μM of DTA (red), 5 (brown), 6 (green), 7 (grey), or 9 (light blue).

AZAPHENOTHIAZINES AND AZAPHENOXAZINES AS ANTIOXIDANTS

CROSS-REFERENCE TO RELATED APPLICATION

This application is a 371 of PCT/CA2018/050314 filed Mar. 15, 2018 which claims benefit of 62/472,812 filed Mar. 17, 2017.

FIELD

The present disclosure relates generally to antioxidants. More particularly, the present disclosure relates to lubricating compositions comprising an antioxidant.

BACKGROUND

Antioxidants are compounds that can retard oxidation, and thus are useful as additives to increase the stability and lifespan of one or more organic substrates that are subject to oxidative degradation. Such degradation may occur under ambient conditions or may be induced by heat and/or light. Antioxidants can be useful as protective additives in engine oils, automatic transmission fluids, industrial utility grade oils, compressor oils, gear and hydraulic oils, biodiesels, plastics, rubber and rubber like substances, unsaturated monomers, elastomers, adhesives, cosmetics preparations, coatings, dyes, inks, and pharmaceutical preparations.

Antioxidants are also useful as additives present during the processing or synthesis of many organic substrates, for example as additives during polymerization, because of the ability of the antioxidant to scavenge free radicals, and thus improve the yield, stability and longevity of the desired resulting product.

Antioxidants are commonly added to organic substrates such as combustion engine lubricating oils, to assist in reducing unwanted oxidation, and increasing performance standards. Combustion engine lubricants oxidize readily at the high operating temperatures of an engine, and in turn, have diminished lubricating capacity as the viscosity of the lubricant increases, and the oxidation products accumulate to form deposits, which in turn leads to greater wear on engine parts.

There remains a need for antioxidants.

SUMMARY

In one aspect, there is provided a compound of Formula (I)

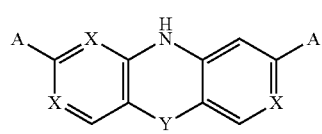

(I)

wherein:
X is CH or N, wherein at least one X is N, wherein at least two X are N, Y is S, or O,
A is either H or an electron donating group.
In one example, said electron donating group is a hydrocarbon group, an aryl group, an alkyl group, an alkoxy group, an amine group, a monosubstituted amine, or a disubstituted amine.

In one aspect there is provided a compound of Formula (II)

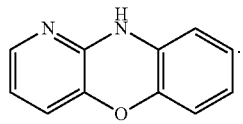

(II)

In one aspect there is provided a compound of Formula (III)

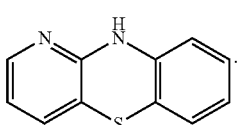

(III)

In one aspect there is provided a compound of Formula (IV)

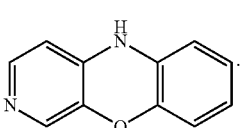

(IV)

In one aspect there is provided a compound of Formula (V)

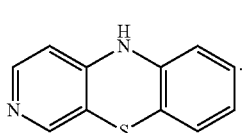

(V)

In one aspect there is provided a compound of Formula (VI)

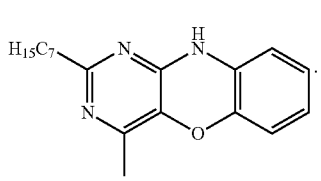

(VI)

In one aspect there is provided a compound of Formula (VII)

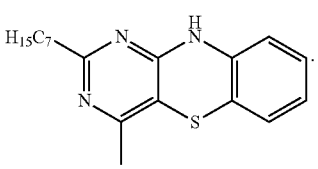

(VII)

In one aspect there is provided a compound of Formula (VIII)

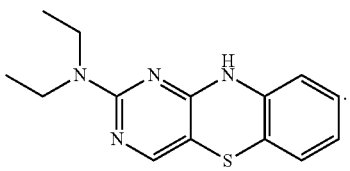

In one aspect there is provided a compound of Formula (IX)

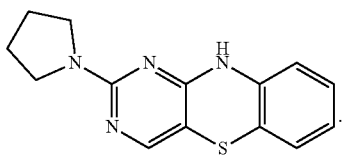

In one aspect there is provided a compound of Formula (X)

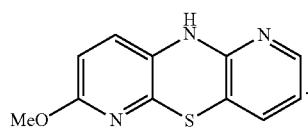

In one aspect there is provided a compound of Formula (XI)

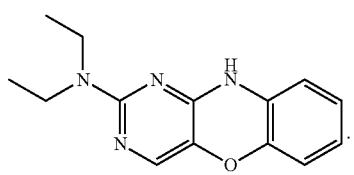

In one aspect there is provided a lubricant composition, comprising:
an oil of lubricating viscosity, and
a compound of any one of claims 1 to 12.

In one example, said oil of lubricating viscosity comprises a natural oil, a synthetic oil, or a mixture of a natural oil and a synthetic oil.

In one example, said oil of lubricating viscosity comprises an API base oil of Group I, Group II, Group III, Group IV, or Group V.

In one example, the lubricant composition further comprising an additive.

In one example, said additive comprises one or more of a metal deactivator, a detergent, a friction modifier, an antiwear agent, a rust inhibitor, a dispersant, a viscosity index improver, an extreme pressure agent, an additional antioxidant, a foam inhibitors, a pour point depressant, a seal swelling agent.

In one aspect there is provided a use of a lubricant composition according to any one of claims 13 to 17 as a lubricant for a combustion engine.

In one aspect there is provided a method of forming a lubricant composition, comprising: combining an oil of lubricating viscosity, providing with an antioxidant according to any one of claims 1 to 12.

In one example, said oil of lubricating viscosity comprises a natural oil, a synthetic oil, or a mixture of a natural oil and a synthetic oil.

In one example, said oil of lubricating viscosity comprises an API base oil of Group I, Group II, Group III, Group IV, or Group V.

In one example, the method further comprising combining an additive.

In one example, said additive comprises one or more of a metal deactivator, a detergent, a friction modifier, an antiwear agent, a rust inhibitor, a dispersant, a viscosity index improver, an extreme pressure agent, an additional antioxidant, a foam inhibitors, a pour point depressant, a seal swelling agent.

In one aspect there is provided a kit comprising: an oil of lubricating viscosity, and an antioxidant according to any one of claims 1 to 12.

In one example, said oil of lubricating viscosity comprises a natural oil, a synthetic oil, or a mixture of a natural oil and a synthetic oil.

In one example, said oil of lubricating viscosity comprises an API base oil of Group I, Group II, Group III, Group IV, or Group V.

In one example, the kit further comprising combining an additive.

In one example, said additive comprises one or more of a metal deactivators, viscosity modifiers, detergents, friction modifiers, antiwear agents, rust inhibitors/corrosion inhibitors, dispersants, dispersant viscosity modifiers, viscosity index improvers, extreme pressure agents, additional antioxidants, foam inhibitors.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
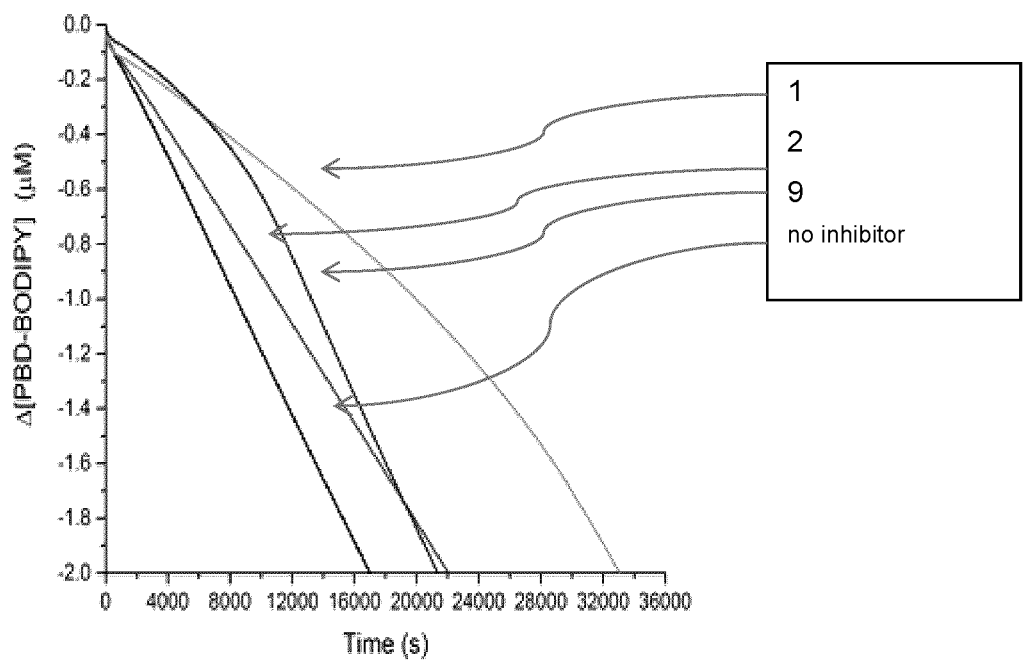
FIG. 1 is a graph depicting co-autoxidation of 2.8M hexadecane and 10 μM PBD-BODIPY at 70° C. in PhCl, initiated by 87 mM tBu$_2$O$_2$, and inhibited by 0.6 μM 1, 2, or 9.
Figure 2:
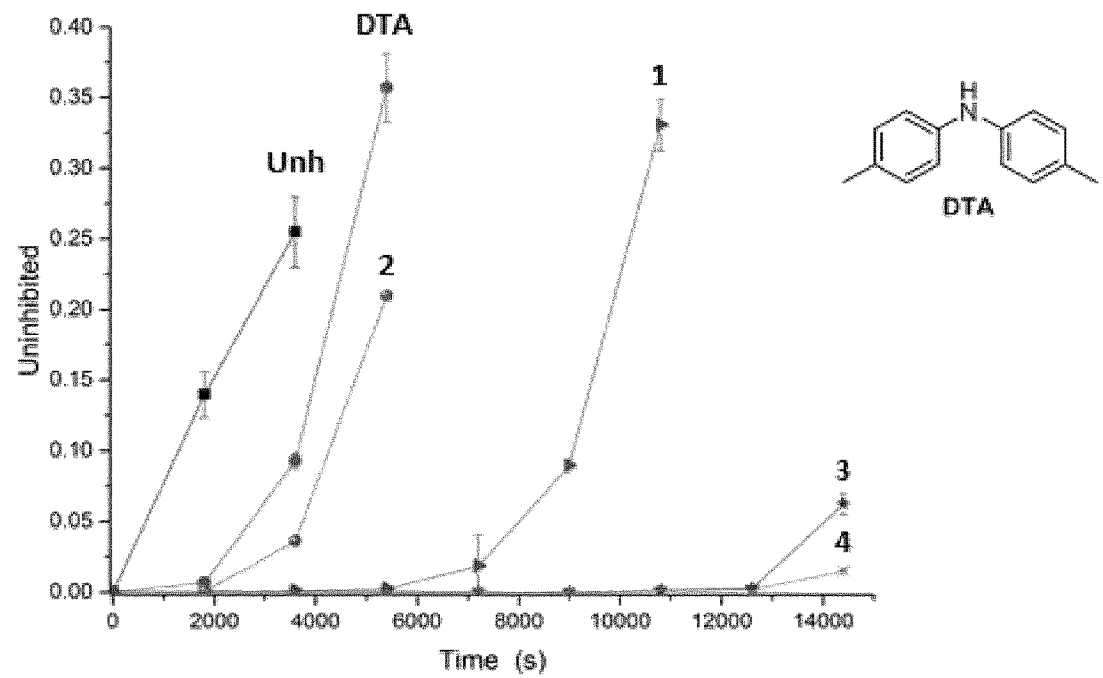
FIG. 2 is a graph depicting hydroperoxide formation in n-hexadecane autoxidations at 160° C., uninhibited (black), and inhibited with 100 μM of DTA, 1, 2, 3, and 4.
Figure 3:
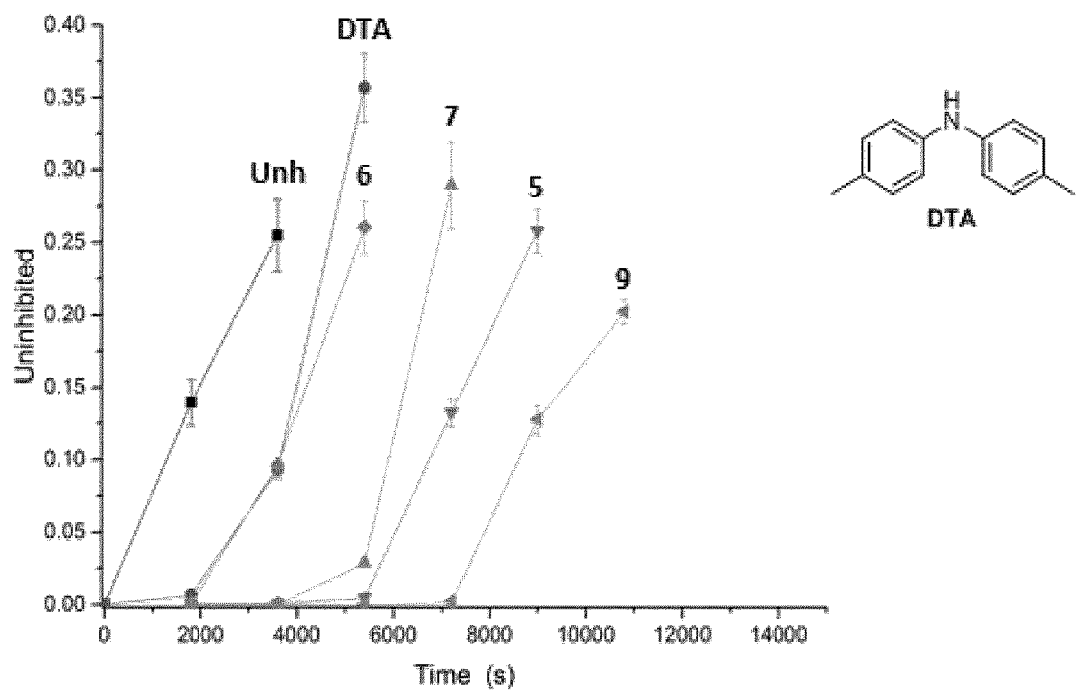
FIG. 3 is a graph depicting hydroperoxide formation in n-hexadecane autoxidations at 160° C., uninhibited, and inhibited with 100 μM of DTA, 5, 6, 7, or 9.

Generally, the present disclosure provides compounds, compositions, their methods of preparation, and uses thereof, wherein said compounds are antioxidants.

Compounds

In one aspect, there is provided a compound of Formula (I)

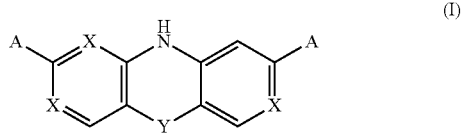

wherein:

X is CH or N, in one example at least one X is N, in one example at least two X are N, Y is S, or O, A is H or an electron donating group.

As used herein, the term "hydrocarbon," used alone or in combination, refers to a linear, branched or cyclic organic moiety comprising carbon and hydrogen, for example, alkyl, alkene, alkyne, and aryl, which may each be optionally substituted. A hydrocarbon may, for example, comprise about 1 to about 100 carbons, about 1 to about 60 carbons, about 1 to about 10, about 1 to about 9 carbons, about 1 to about 8 carbons, about 1 to about 6 carbons, about 1 to about 4 carbons, or about 1 to about 3 carbons. In some embodiments, hydrocarbon comprises 10 carbons, 9 carbons, 8 carbons, 7 carbons, 6 carbons, 5 carbons, 4 carbons, 3 carbons, 2 carbons, or 1 carbon. In the case of polymers having hydrocarbon backbones and/or branches, the number of carbons could be much higher.

The term "aryl", used alone or in combination, means an aromatic carbocyclic moiety of up to 60 carbon atoms, which may be a single ring (monocyclic) or multiple rings fused together (e.g., bicyclic or tricyclic fused ring systems). In some embodiments, aryl has up to 60 carbon atoms, up to 40 carbon atoms, up 20 carbon atoms, up to 12 carbon atoms, up to 10 carbon atoms, up to 9 carbon atoms, or up to 6 carbon atoms. Any suitable ring position of the aryl moiety may be covalently linked to the defined chemical structure.

The term "substituted aryl" means an aryl, as defined above, having from one to multiple substituents.

The term "alkyl", used alone or in combination, means a straight or branched hydrocarbon group. In some embodiments, alkyl has about 1 to about 60 carbons, about 1 to about 40 carbons, about 1 about 30 carbons, about 1 to about 20, 1 to about 10, 1 to about 8 or 1 to about 6 carbons. Examples of branched or unbranched $C_1$-$C_8$ alkyl groups include, for example, methyl, ethyl, propyl, isopropyl, butyl, isobutyl, tert-butyl, the isomeric pentyls, the isomeric hexyls, the isomeric heptyls, and the isomeric octyls.

The term "heteroaryl", used alone or in combination, means a radical derived from an aromatic carbocyclic moiety of up to 60 ring atoms, comprising carbon atom ring atoms and one or more heteroatom ring atoms. Each heteroatom is independently selected from nitrogen, which can be oxidized (e.g., N(O)) or quaternized; oxygen; and sulfur, including sulfoxide and sulfone. The heteroaryl group can be a monocyclic or polycyclic heteroaromatic ring system including but not limited to condensed heterocyclic aromatic rings, and condensed carbocyclic and heterocyclic aromatic rings. The point of attachment of a heteroaryl group to another group may be at either a carbon atom or a heteroatom of the heteroaryl group.

The term "substituted heteroaryl" means a heteroaryl, as defined above, having from one to multiple substituents.

The term "aryloxy", used alone or in combination, means the group —O-aryl, wherein the aryl group is as defined above. The term "heteroaryloxy", used alone or in combination, means the group —O-heteroaryl, wherein the heteroaryl group is as defined above.

The term "alkoxy", used alone or in combination, means the group —O-alkyl, wherein the alkyl group is as defined above. Examples include, for example, methoxy, ethoxy, n-propyloxy, and iso-propyloxy.

The term "electron donating group" as used herein includes, but is not limited to, an H atom, a hydrocarbon group, an aryl group, an alkyl group, an alkoxy group ($OR^4$), an amine group, a monosubstituted amine ($NHR^5$), and a disubstituted amine ($NR^5R^6$). The electron-donating strength of the alkoxy or amine group comes largely from the lone pairs of electrons on the O and N atoms, respectively, such that each of $R^4$, $R^5$ and $R^6$ can be a hydrogen or a saturated or unsaturated branched or straight chain hydrocarbon moiety and/or may include one or more cycloaliphatic groups and/or one or more aromatic hydrocarbons, or a combination thereof, while not detracting from the electron donating characteristic of the alkoxy or amine group. In some examples, the electron donating group comprises a lone pair of electrons, on for example, a nitrogen atom (N), a phosphorous atom (P), an oxygen atom (O), or a sulfur atom (S).

The term "cycloaliphatic" as used herein includes a saturated or unsaturated carbocyclic moiety comprising mono- or bicyclic rings. Cycloaliphatic includes a 3- to 7-membered saturated carbocyclic moiety. Examples of cycloaliphatic moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

Additional examples of the compound described herein include, but are not limited to:

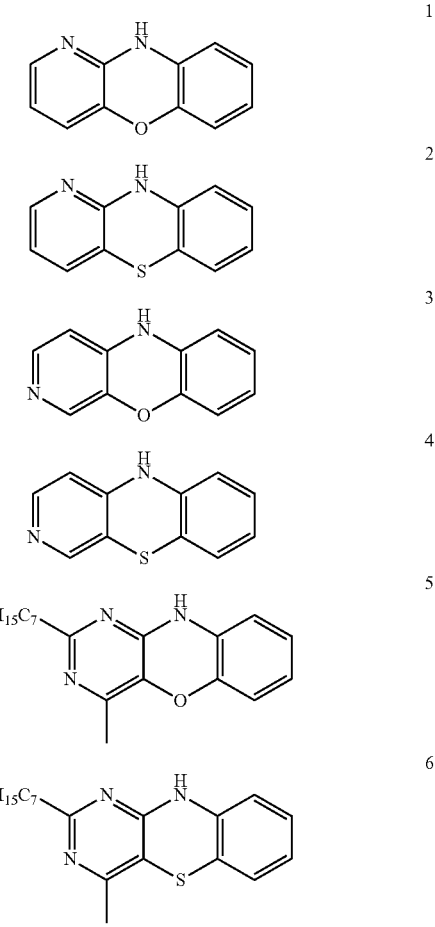

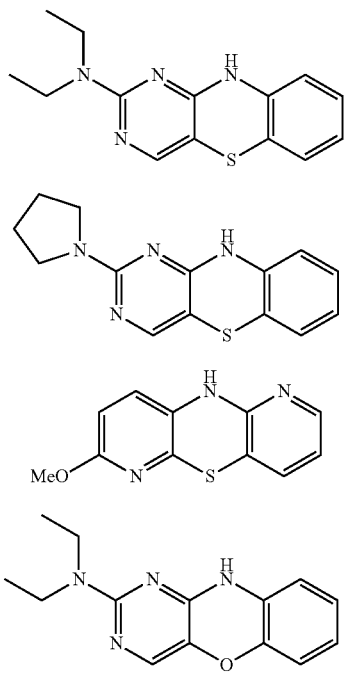

In one aspect, the compounds described herein are antioxidants.

In one aspect, the compounds described herein are antioxidants for use in a lubricating composition.

In one aspect, the compounds described herein are antioxidants for use in a lubricating composition for a combustion engine.

In one aspect, an effective amount of the compounds described herein are for use in a lubricating composition for a combustion engine.

As used herein, the term "effective amount" refers to the amount of compound (or compounds) which is added to an oil of lubricating viscosity so as to provide activity. In some examples, the "effective amount" is an amount of compound(s) sufficient to reduce the level of degradation of an oil of lubricating viscosity when compared to the level of degradation of the oil of lubricating viscosity in the absence of said compound(s). In some examples, an "effective amount" of a compound described herein is an amount sufficient to enable the compound(s) to scavenge one or more free radicals existing, or formed within a lubricating composition.

Lubricating Composition

There is described herein a lubricating composition comprising an oil of lubricating viscosity, an antioxidant (also referred to as a compound herein above) as described above and herein, and optionally comprising one or more additives (also referred to as performance additives). In some examples, the lubricating composition is for use in a combustion engine.

In some examples, a fully-formulated lubricating oil will contain one or more additives.

As used herein, the terms "oil composition," "lubrication composition," "lubricating oil composition," "lubricating oil," "lubricant composition," "lubricating composition," "fully formulated lubricant composition," "lubricant," "crankcase oil," "crankcase lubricant," "engine oil," "engine lubricant," "motor oil," and "motor lubricant" are considered synonymous, fully interchangeable terminology referring to the finished lubrication product comprising an oil of lubricating viscosity, an antioxidant, and optionally a performance additives.

In some examples, the antioxidant is present in an amount of about 0.1 to about 40 percent by weight of the lubricating composition.

In some examples, the antioxidant is present in an amount of less than about 40, 30, 25, 20, 15, 10, 5, 2, 1.5, 1, 0.9, 0.8, 0.7, 0.6, 0.5, 0.4, 0.3, 0.2, or 0.1 percent by weight of the lubricating composition.

As used herein, the term "percent by weight", unless expressly stated otherwise, means the percentage the recited component represents to the weight of the entire composition.

Additives

The lubricating composition can include one or more additives, also referred to as performance additives, to improve various chemical and/or physical properties. Additives may be selected to perform one or more functions required of a lubricating fluid. Further, one or more of the mentioned additives may be multifunctional and provide functions in addition to or other than the function prescribed herein.

Additives include, but are not limited to, metal deactivators, detergents, friction modifiers, antiwear agents, rust inhibitors, dispersants, viscosity index improvers, extreme pressure agents, additional antioxidants, foam inhibitors, pour point depressants, seal swelling agents. One or more of the additives may be ash-including or ash-less.

Combustion Engine

A lubricating composition as described herein, combinations of components, or individual components of the present description, are suitable for use in various types of internal combustion engines. Engine types may include, but are not limited to, heavy duty diesel, passenger car, light duty diesel, medium speed diesel, or marine engines. An internal combustion engine may be a diesel fueled engine, a gasoline fueled engine, a natural gas fueled engine, a biofueled engine, a mixed diesel/biofuel fueled engine, a mixed gasoline/biofuel fueled engine, an alcohol fueled engine, a mixed gasoline/alcohol fueled engine, a compressed natural gas (CNG) fueled engine, or mixtures thereof. An internal combustion engine may also be used in combination with an electrical or battery source of power. An engine so configured is commonly known as a hybrid engine. The internal combustion engine may be a 2-stroke, 4-stroke, or rotary engine. Suitable internal combustion engines include marine diesel engines, aviation piston engines, low-load diesel engines, and motorcycle, automobile, locomotive, and truck engines.

The internal combustion engine may contain components of one or more of an aluminum-alloy, lead, tin, copper, cast iron, magnesium, ceramics, stainless steel, composites, and/or mixtures thereof. The components may be coated, for example, with a diamond-like carbon coating, a lubricated coating, a phosphorus-containing coating, molybdenum-containing coating, a graphite coating, a nano-particle-containing coating, and/or mixtures thereof. The aluminum-alloy may include aluminum silicates, aluminum oxides, or other ceramic materials. In one embodiment the aluminum-alloy is an aluminum-silicate surface. As used herein, the term "aluminum alloy" is intended to be synonymous with "aluminum composite" and to describe a component or surface comprising aluminum and another component intermixed or reacted on a microscopic or nearly microscopic level, regardless of the detailed structure thereof. This would include any conventional alloys with metals other than aluminum as well as composite or alloy-like structures with non-metallic elements or compounds such with ceramic-like materials.

The lubricating composition for an internal combustion engine may be suitable for any engine lubricant irrespective of the sulfur, phosphorus, or sulfated ash content.

Oil of Lubricating Viscosity

An oil of lubricating viscosity, which may also be referred to as "base stock" or "base oil", is the primary liquid constituent of a lubricant, into which an antioxidant as described herein is blended, optionally with performance additives, and optionally with other oils, for example to produce a final lubricant (or lubricating composition). A base oil is useful for making concentrates as well as for making lubricating oil compositions therefrom, and may be selected from natural (vegetable, animal or mineral) and synthetic lubricating oils and mixtures thereof.

In one example, the base stock groups are defined in the American Petroleum Institute (API) publication "Engine Oil Licensing and Certification System", Industry Services Department. Typically, the base stock will have a viscosity of 3-12, in some examples 4-10, in other examples 4.5-8, mm2/s (cSt) at 100° C.

In some examples, the base stocks and base oils are the same as those found in the American Petroleum Institute (API) publication "Engine Oil Licensing and Certification System", Industry Services Department, Fourteenth Edition. For example:

A) Group I base stocks contain less than 90 percent saturates and/or greater than 0.03 percent sulphur and have a viscosity index greater than or equal to 80 and less than 120 using the test methods specified in Table E-1.

B) Group II base stocks contain greater than or equal to 90 percent saturates and less than or equal to 0.03 percent sulphur and have a viscosity index greater than or equal to 80 and less than 120 using the test methods specified in Table E-1.

C) Group III base stocks contain greater than or equal to 90 percent saturates and less than or equal to 0.03 percent sulphur and have a viscosity index greater than or equal to 120 using the test methods specified in Table E-1.

D) Group IV base stocks are polyalphaolefins (PAO).

E) Group V base stocks include all other base stocks not included in Group I, III, or IV.

It will be appreciated that other oils of lubricating viscosity may be included in the lubricating oil composition.

Natural oils include animal and vegetable oils (e.g. castor and lard oil), liquid petroleum oils and hydrorefined, solvent-treated mineral lubricating oils of the paraffinic, naphthenic and mixed paraffinic-naphthenic types. Oils of lubricating viscosity derived from coal or shale are also useful base oils.

Synthetic lubricating oils include hydrocarbon oils such as polymerized and interpolymerized olefins (e.g. polybutylenes, polypropylenes, propylene-isobutylene copolymers, chlorinated polybutylenes, poly(1-hexenes), poly(1-octenes), poly(1-decenes)); alkylbenzenes (e.g. dodecylbenzenes, tetradecylbenzenes, dinonylbenzenes, di(2-ethylhexyl)benzenes); polyphenols (e.g. biphenyls, terphenyls, alkylated polyphenols); and alkylated diphenyl ethers and alkylated diphenyl sulfides and the derivatives, analogues and homologues thereof.

Esters useful as synthetic oils also include those made from C5 to C12 monocarboxylic acids and polyols, and polyol ethers such as neopentyl glycol, trimethylolpropane, pentaerythritol, dipentaerythritol and tri pentaerythritol.

Unrefined, refined and re-refined oils can be used in the compositions of the present invention.

Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be unrefined oil.

Refined oils are similar to the unrefined oils except they have been further treated in one or more purification steps to improve one or more properties. Many such purification techniques, such as distillation, solvent extraction, acid or base extraction, filtration and percolation are known to those skilled in the art. Re-refined oils are obtained by processes similar to those used to obtain refined oils applied to refined oils which have been already used in service. Such re-refined oils are also known as reclaimed or reprocessed oils and often are additionally processed by techniques for approval of spent additive and oil breakdown products.

Other examples of base oil are gas-to-liquid ("GTL") base oils, i.e. the base oil may be an oil derived from Fischer-Tropsch synthesised hydrocarbons made from synthesis gas containing $H_2$ and CO using a Fischer-Tropsch catalyst. These hydrocarbons typically require further processing in order to be useful as a base oil. For example, they may, by methods known in the art, be hydroisomerized; hydrocracked and hydroisomerized; dewaxed; or hydroisomerized and dewaxed.

The composition of the base oil will depend upon the particular application of the lubricating oil composition and the oil formulator will chose the base oil to achieve desired performance characteristics at reasonable cost.

As discussed above, the oil of lubricating viscosity comprises an antioxidant, and optional performance additives. This preparation may be accomplished by adding the additives directly to the oil or by adding them in the form of a concentrate thereof to disperse or dissolve the additive. Additives may be added to the oil by any method known to those skilled in the art, either before, at the same time as, or after addition of other additives.

Friction Modifiers

Friction modifier include, but are not limited to, metal containing and metal-free friction modifiers and may include, but are not limited to, imidazolines, amides, amines, succinimides, alkoxylated amines, alkoxylated ether amines, amine oxides, amidoamines, nitriles, betaines, quaternary amines, imines, amine salts, amino guanidines, alkanolamides, phosphonates, metal-containing compounds, glycerol esters, sulfurized fatty compounds and olefins, sunflower oil and other naturally occurring plant or animal oils, dicarboxylic acid esters, esters or partial esters of a polyol and one or more aliphatic or aromatic carboxylic acids, and the like.

Friction modifiers may contain hydrocarbyl groups that are selected from straight chain, branched chain, or aromatic hydrocarbyl groups or mixtures thereof, and may be saturated or unsaturated. The hydrocarbyl groups may be composed of carbon and hydrogen or hetero atoms such as sulfur or oxygen. The hydrocarbyl groups may range from about 12 to about 25 carbon atoms. In one embodiments the friction modifier may be a long chain fatty acid ester. In an embodiment the long chain fatty acid ester may be a mono-ester, or a di-ester, or a (tri)glyceride. The friction modifier may be a long chain fatty amide, a long chain fatty ester, a long chain fatty epoxide derivative, or a long chain imidazoline.

Viscosity Index Improvers

Viscosity index improvers, also referred to as viscosity modifiers or viscosity improvers, may have that sole function, or may be multifunctional. Multifunctional viscosity modifiers that also function as dispersants are also known.

Viscosity index improvers include, but are not limited to, polyisobutylene, copolymers of ethylene and propylene and higher alpha-olefins, polymethacrylates, polyalkylmethacrylates, methacrylate copolymers, copolymers of an unsaturated dicarboxylic acid and a vinyl compound, inter polymers of styrene and acrylic esters, and partially hydrogenated copolymers of styrene/isoprene, styrene/butadiene, and isoprene/butadiene, as well as the partially hydrogenated homopolymers of butadiene and isoprene and isoprene/divinylbenzene.

Pour Point Depressants

Pour point depressants, also referred to as lube oil flow improvers, lower the minimum temperature at which the fluid will flow or can be poured. Pour point depressants can be selected according to the characteristics of the lubricating oil base oil from any of the known pour point depressants. Pour point depressants include, but are not limited to, C8 to C18 dialkyl fumarate/vinyl acetate copolymers, polyalkylmethacrylates and the like.

Dispersants

Dispersants are well known in the field of lubricants and include ashless-type dispersants and polymeric dispersants. Ashless type dispersants are characterized by a polar group attached to a relatively high molecular weight hydrocarbon chain. Typical ashless dispersants include nitrogen-containing dispersants such as N-substituted long chain alkenyl succinimides, also known as succinimide dispersants. Mixtures of types of succinimide dispersants are also contemplated. Another class of ashless dispersant is high molecular weight esters, prepared by reaction of a hydrocarbyl acylating agent and a polyhydric aliphatic alcohol such as glycerol, pentaerythritol, or sorbitol. Another class of ashless dispersant is Mannich bases. These are materials which are formed by the condensation of a higher molecular weight, alkyl substituted phenol, an alkylene polyamine, and an aldehyde such as formaldehyde. Other dispersants include polymeric dispersant additives, which are generally hydrocarbon-based polymers which contain polar functionality to impart dispersancy characteristics to the polymer. Dispersants can also be post-treated by reaction with any of a variety of agents. Among these are urea, thiourea, dimercaptothiadiazoles, carbon disulfide, aldehydes, ketones, carboxylic acids, hydrocarbon-substituted succinic anhydrides, nitriles, epoxides, boron compounds, and phosphorus compounds.

Extreme Pressure Agent

Extreme pressure agents include, but are not limited to, pressure agents that are soluble in the oil include sulfur- and chlorosulfur-containing extreme pressure agents, chlorinated hydrocarbon extreme pressure agents and phosphorus extreme pressure agents. Examples of such extreme pressure agents include, but are not limited to, chlorinated waxes; organic sulfides and polysulfides such as dibenzyldisulfide, bis(chlorobenzyl) disulfide, dibutyl tetrasulfide, sulfurized methyl ester of oleic acid, sulfurized alkylphenol, sulfurized dipentene, sulfurized terpene, and sulfurized Diels-Alder adducts; phosphosulfurized hydrocarbons such as the reaction product of phosphorus sulfide with turpentine or methyl oleate; phosphorus esters such as the dihydrocarbyl and trihydrocarbyl phosphites, e.g., dibutyl phosphite, diheptyl phosphite, dicyclohexyl phosphite, pentylphenyl phosphite; dipentylphenyl phosphite, tridecyl phosphite, distearyl phosphite and polypropylene substituted phenyl phosphite; metal thiocarbamates such as zinc dioctyldithiocarbamate and barium heptylphenol diacid; amine salts of alkyl and dialkylphosphoric acids, including, for example, the amine salt of the reaction product of a dialkyldithiophosphoric acid with propylene oxide; and mixtures thereof.

Seal Swelling Agents

Seal swell agents include, but are not limited to, sulfolene derivatives.

Metal Deactivators

Metal deactivators include, but are not limited to, derivatives of benzotriazoles (typically tolyltriazole), 1,2,4-triazoles, benzimidazoles, 2-alkyldithiobenzimidazoles or 2-alkyldithiobenzothiazoles. The metal deactivators may also be described as corrosion inhibitors.

Rust Inhibitors

Rust inhibitors include, but are not limited to of petroleum sulphonates, alkylbenzene sulphonates, dinonylnaphthalene sulphonates, metal salts of sulphonates, amine salts of sulphonates, zinc naphthenate, alkenylsuccinate esters and polyhydric alcohol esters.

Detergents

Examples of detergents include, but are not limited to neutral, low based, or overbased detergents, and mixtures thereof. Suitable detergent substrates include phenates, sulfur containing phenates, sulfonates, calixarates, salixarates, salicylates, carboxylic acids, phosphorus acids, mono- and/or di-thiophosphoric acids, alkyl phenols, sulfur coupled alkyl phenol compounds, or methylene bridged phenols. The detergent substrate may be salted with an alkali or alkaline earth metal such as, but not limited to, calcium, magnesium, potassium, sodium, lithium, barium, or mixtures thereof. In some embodiments, the detergent is free of barium. A suitable detergent may include alkali or alkaline earth metal salts of petroleum sulfonic acids and long chain mono- or di-alkylarylsulfonic acids with the aryl group being benzyl, tolyl, and xylyl. Examples of suitable detergents include, but are not limited to, calcium phenates, calcium sulfur containing phenates, calcium sulfonates, calcium calixarates, calcium salixarates, calcium salicylates, calcium carboxylic acids, calcium phosphorus acids, calcium mono- and/or di-thiophosphoric acids, calcium alkyl phenols, calcium sulfur coupled alkyl phenol compounds, calcium methylene bridged phenols, magnesium phenates, magnesium sulfur containing phenates, magnesium sulfonates, magnesium calixarates, magnesium salixarates, magnesium salicylates, magnesium carboxylic acids, magnesium phosphorus acids, magnesium mono- and/or di-thiophosphoric acids, magnesium alkyl phenols, magnesium sulfur coupled alkyl phenol compounds, magnesium methylene bridged phenols, sodium phenates, sodium sulfur containing phenates, sodium sulfonates, sodium calixarates, sodium salixarates, sodium salicylates, sodium carboxylic acids, sodium phosphorus acids, sodium mono- and/or di-thiophosphoric acids, sodium alkyl phenols, sodium sulfur coupled alkyl phenol compounds, or sodium methylene bridged phenols.

Overbased detergent additives are well known in the art and may be alkali or alkaline earth metal overbased detergent additives. Such detergent additives may be prepared by reacting a metal oxide or metal hydroxide with a substrate and carbon dioxide gas. The substrate is typically an acid, for example, an acid such as an aliphatic substituted sulfonic acid, an aliphatic substituted carboxylic acid, or an aliphatic substituted phenol.

The terminology "overbased" relates to metal salts, such as metal salts of sulfonates, carboxylates, and phenates, wherein the amount of metal present exceeds the stoichiometric amount. Such salts may have a conversion level in excess of 100% (i.e., they may comprise more than 100% of the theoretical amount of metal needed to convert the acid to its "normal," "neutral" salt). The expression "metal ratio," often abbreviated as MR, is used to designate the ratio of total chemical equivalents of metal in the overbased salt to chemical equivalents of the metal in a neutral salt according to known chemical reactivity and stoichiometry. In a normal or neutral salt, the metal ratio is one and in an overbased salt, MR, is greater than one. They are commonly referred to as overbased, hyperbased, or superbased salts and may be salts of organic sulfur acids, carboxylic acids, or phenols.

Examples of suitable overbased detergents include, but are not limited to, overbased calcium phenates, overbased calcium sulfur containing phenates, overbased calcium sulfonates, overbased calcium calixarates, overbased calcium salixarates, overbased calcium salicylates, overbased calcium carboxylic acids, overbased calcium phosphorus acids, overbased calcium mono- and/or di-thiophosphoric acids, overbased calcium alkyl phenols, overbased calcium sulfur coupled alkyl phenol compounds, overbased calcium methylene bridged phenols, overbased magnesium phenates, overbased magnesium sulfur containing phenates, overbased magnesium sulfonates, overbased magnesium calixarates, overbased magnesium salixarates, overbased magnesium salicylates, overbased magnesium carboxylic acids, overbased magnesium phosphorus acids, overbased magnesium mono- and/or di-thiophosphoric acids, overbased magnesium alkyl phenols, overbased magnesium sulfur coupled alkyl phenol compounds, or overbased magnesium methylene bridged phenols.

Antiwear Agent

Examples antiwear agents include, but are not limited to, titanium compounds, tartrates, tartrim ides, oil soluble amine salts of phosphorus compounds, sulphurised olefins, metal dihydrocarbyldithiophosphates (such as zinc dialkyldithiophosphates), phosphites (such as dibutyl phosphite), phosphonates, thiocarbamate-containing compounds, such as thiocarbamate esters, thiocarbamate amides, thiocarbamic ethers, alkylene-coupled thiocarbamates, and bis(S-alkyldithiocarbamyl) disulphides. The antiwear agent may in one embodiment include a tartrate, or tartrimide.

Foam Inhibitor

Foam inhibitors include, but are not limited to, polysiloxanes, copolymers of ethyl acrylate and 2-ethylhexylacrylate and optionally vinyl acetate; demulsifiers including fluorinated polysiloxanes, trialkyl phosphates, polyethylene glycols, polyethylene oxides, polypropylene oxides and (ethylene oxide-propylene oxide) polymers.

Additional Antioxidants

The lubricating oil compositions herein also may optionally contain one or more additional antioxidant, in addition to the antioxidants as described herein above.

Such additional antioxidant compounds are known and include for example, phenates, phenate sulfides, sulfurized olefins, phosphosulfurized terpenes, sulfurized esters, aromatic amines, alkylated diphenylamines (e.g., nonyl diphenylamine, di-nonyl diphenylamine, octyl diphenylamine, di-octyl diphenylamine), phenyl-alpha-naphthylamines, alkylated phenyl-alpha-naphthylamines, hindered non-aromatic amines, phenols, hindered phenols, oil-soluble molybdenum compounds, macromolecular antioxidants, or mixtures thereof. Antioxidant compounds may be used alone or in combination.

The hindered phenol antioxidant may contain a secondary butyl and/or a tertiary butyl group as a sterically hindering group. The phenol group may be further substituted with a hydrocarbyl group and/or a bridging group linking to a second aromatic group. Examples of suitable hindered phenol antioxidants include 2,6-di-tert-butylphenol, 4-methyl-2,6-di-tert-butylphenol, 4-ethyl-2,6-di-tert-butylphenol, 4-propyl-2,6-di-tert-butylphenol or 4-butyl-2,6-di-tert-butylphenol, or 4-dodecyl-2,6-di-tert-butylphenol. In one embodiment the hindered phenol antioxidant may be an ester or an addition product derived from 2,6-di-tert-butylphenol and an alkyl acrylate, wherein the alkyl group may contain about 1 to about 18, or about 2 to about 12, or about 2 to about 8, or about 2 to about 6, or about 4 carbon atoms. Another commercially available hindered phenol antioxidant may be an ester.

In some examples, the additional antioxidant includes diarylamines and high molecular weight phenols.

In some example, the additional antioxidant includes olefins that may be sulfurized to form a sulfurized olefin include propylene, butylene, isobutylene, polyisobutylene, pentene, hexene, heptene, octene, nonene, decene, undecene, dodecene, tridecene, tetradecene, pentadecene, hexadecene, heptadecene, octadecene, nonadecene, eicosene or mixtures thereof. In one embodiment, hexadecene, heptadecene, octadecene, nonadecene, eicosene or mixtures thereof and their dimers, trimers and tetramers are especially useful olefins. Alternatively, the olefin may be a Diels-Alder adduct of a diene such as 1,3-butadiene and an unsaturated ester, such as, butylacrylate.

Another class of sulfurized olefin includes sulfurized fatty acids and their esters. The fatty acids are often obtained from vegetable oil or animal oil and typically contain about 4 to about 22 carbon atoms. Examples of suitable fatty acids and their esters include triglycerides, oleic acid, linoleic acid, palmitoleic acid or mixtures thereof. Often, the fatty acids are obtained from lard oil, tall oil, peanut oil, soybean oil, cottonseed oil, sunflower seed oil or mixtures thereof. Fatty acids and/or ester may be mixed with olefins, such as α-olefins.

In some examples, the additional antioxidant is an aminic antioxidant, and includes for example, alkylated diphenylamines, phenyl-α-naphthylamines, phenyl-β-naphthylamines and alkylated α-naphthylamines.

In some example, the aminic antioxidants include, but are not limited to, dialkyldiphenylamines such as p,p'-dioctyl-diphenylamine, p,p'-di-α-methylbenzyl-diphenylamine and N-p-butylphenyl-N-p'-octylphenylamine, monoalkyldiphenylamines such as mono-t-butyldiphenylamine and mono-octyldiphenylamine, bis(dialkylphenyl)amines such as di-(2,4-diethylphenyl)amine and di(2-ethyl-4-nonylphenyl)amine, alkylphenyl-1-naphthylamines such as octylphenyl-1-naphthylamine and n-t-dodecylphenyl-1-naphthylamine, 1-naphthylamine, arylnaphthylamines such as phenyl-1-naphthylamine, phenyl-2-naphthylamine, N-hexylphenyl-2-naphthylamine and N-octylphenyl-2-naphthylamine, phenylenediamines such as N,N'-diisopropyl-p-phenylenediamine and N,N'-diphenyl-p-phenylenediamine, and phenothiazines such as phenothiazine and 3,7-dioctylphenothiazine.

In some example, phenolic antioxidants include, but are not limited to, C7-C9 branched alkyl esters of 3,5-bis(1,1-dimethyl-ethyl)-4-hydroxy-benzenepropanoic acid, 2-t-butylphenol, 2-t-butyl-4-methylphenol, 2-t-butyl-5-methylphenol, 2,4-di-t-butylphenol, 2,4-dimethyl-6-t-butylphenol, 2-t-butyl-4-methoxyphenol, 3-t-butyl-4-methoxyphenol, 2,5-di-t-butylhydroquinone, 2,6-di-t-butyl-4-alkylphenols such as 2,6-di-t-butylphenol, 2,6-di-t-butyl-4-methylphenol and 2,6-di-t-butyl-4-ethylphenol, 2,6-di-t-butyl-4-alkoxyphenols such as 2,6-di-t-butyl-4-methoxyphenol and 2,6-di-t-butyl-4-ethoxyphenol, 3,5-di-t-butyl-4-hydroxybenzylmercaptooctylacetate, alkyl-3-(3,5-di-t-butyl-4-hydroxyphenyl)propionates such as n-octadecyl-3-(3,5-di-t-butyl-4-hydroxyphenyl)propionate, n-butyl-3-(3,5-di-t-butyl-4-hydroxyphenyl)propionate and 2'-ethylhexyl-3-(3,5-di-t-butyl-4-hydroxyphenyl)propionate, 2,6-d-t-butyl-α-dimethylam ino-p-cresol, 2,2'-methylene-bis(4-alkyl-6-t-butylphenol) such as 2,2'-methylenebis(4-methyl-6-t-butylphenol, and 2,2-methylenebis(4-ethyl-6-t-butylphenol), bisphenols such as 4,4'-butylidenebis(3-methyl-6-t-butylphenol, 4,4'-methylenebis(2,6-di-t-butylphenol), 4,4'-bis(2,6-di-t-butylphenol), 2,2-(di-p-hydroxyphenyl)propane, 2,2-bis(3,5-di-t-butyl-4-hydroxyphenyl)propane, 4,4'-cyclohexylidenebis(2,6-t-butylphenol), hexamethyleneglycol-bis[3-(3,5-di-t-butyl-4-hydroxyphenyl)propionate], triethyleneglycolbis[3-(3-t-butyl-4-hydroxy-5-methylphenyl)propionate], 2,2'-thio-[diethyl-3-(3,5-di-t-butyl-4-hydroxyphenyl)propionate], 3,9-bis{1,1-dimethyl-2-[3-(3-t-butyl-4-hydroxy-5-methylphenyl)propionyloxy]ethyl}2,4,8,10-tetraoxaspiro[5,5]undecane, 4,4'-thiobis(3-methyl-6-t-butylphenol) and 2,2'-thiobis(4,6-di-t-butylresorcinol), polyphenols such as tetrakis[methylene-3-(3,5-di-t-butyl-4-hydroxyphenyl)propionate]methane, 1,1,3-tris(2-methyl-4-hydroxy-5-t-butylphenyl)butane, 1,3,5-trimethyl-2,4,6-tris(3,5-di-t-butyl-4-hydroxybenzyl)benzene, bis-[3,3'-bis(4'-hydroxy-3'-t-butylphenyl)butyric acid]glycol ester, 2-(3',5'-di-t-butyl-4-hydroxyphenyl)methyl-4-(2",4"-di-t-butyl-3"-hydroxyphenyl)methyl-6-t-butylphenol and 2,6-bis(2'-hydroxy-3'-t-butyl-5'-methylbenzyl)-4-methylphenol, and p-t-butylphenol-formaldehyde condensates and p-t-butylphenol-acetaldehyde condensates.

Additive Package

As used herein, the terms "additive package," "additive concentrate," "additive composition," "engine oil additive package," "engine oil additive concentrate," "crankcase additive package," "crankcase additive concentrate," "motor oil additive package," "motor oil concentrate," are considered synonymous, fully interchangeable terminology referring the portion of the lubricating composition excluding the amount of base oil stock mixture. The additive package may or may not include the viscosity index improver or pour point depressant.

The individual additives may be incorporated into a base stock in any convenient way. Thus, each of the components can be added directly to the base stock or base oil blend by dispersing or dissolving it in the base stock or base oil blend at the desired level of concentration.

Method of the invention are conveniently practiced by providing the compounds and/or compositions used in such method in the form of a kit. Such kit preferably contains the composition. Such a kit preferably contains instructions for the use thereof.

To gain a better understanding of the invention described herein, the following examples are set forth. It should be understood that these examples are for illustrative purposes only. Therefore, they should not limit the scope of this invention in anyway.

EXAMPLES

Effect of Nitrogen Incorporation

| | BDL (kcal/mol) | IP (kcal/mol) |
|---|---|---|
| 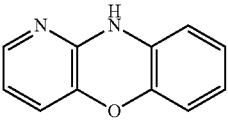 [SMILES: c1ccc2c(c1)Nc1ncccc1O2] | 81.2 | 164.0 |
| 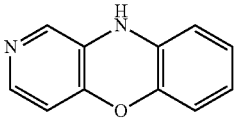 [SMILES: c1ccc2c(c1)Nc1cnccc1O2] | 75.7 | 167.1 |
| 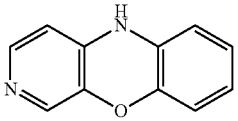 [SMILES: c1ccc2c(c1)Nc1ccncc1O2] | 77.3 | 168.6 |
| 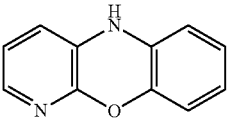 [SMILES: c1ccc2c(c1)Nc1cccnc1O2] | 74.7 | 164.2 |
| 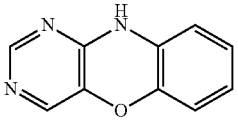 [SMILES: c1ccc2c(c1)Nc1ncncc1O2] | 83.2 | 173.6 |
| 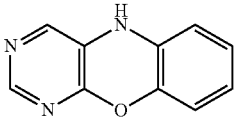 [SMILES: c1ccc2c(c1)Nc1cncnc1O2] | 75.5 | 171.8 |
| 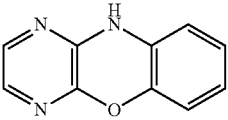 [SMILES: c1ccc2c(c1)Nc1nccnc1O2] | 81.5 | 170.5 |
| 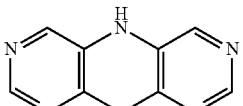 | 75.4 | 184.5 |

Effect of Ring Structure on Retro-Carbonyl-Ene Turnover
| | $\Delta H^\ddagger$ (kcal/mol) | $\Delta G^\ddagger$ (kcal/mol) |
|---|---|---|
| 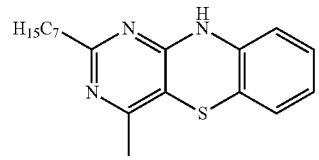 | 33.4 | 35.8 |
| 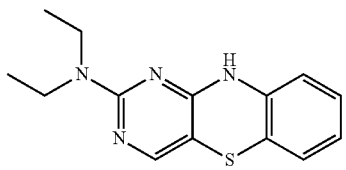 | 28.0 | 28.4 |
| 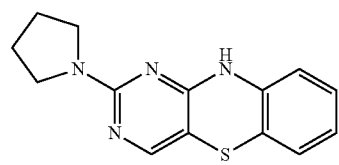 | 32.9 | 33.6 |
Representative Structures
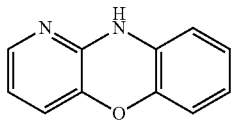
1
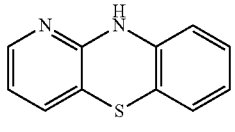
2
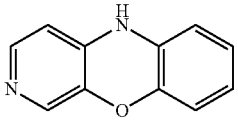
3
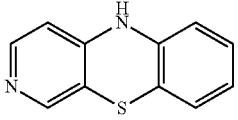
4
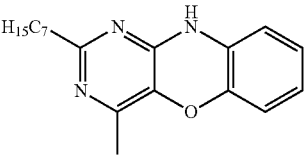
5
-continued
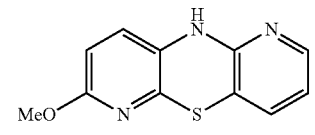
6
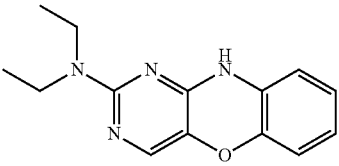
7
8
9
10
SYNTHETIC SCHEMES
Synthesis of 1[1]
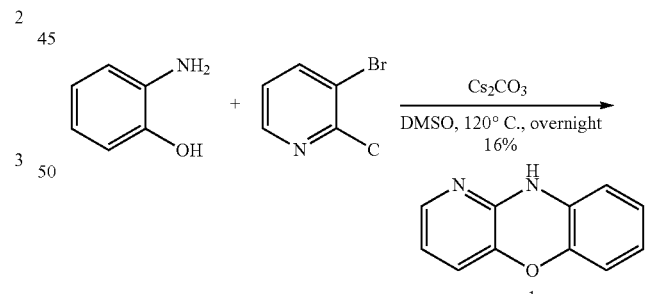
Synthesis of 2[2]
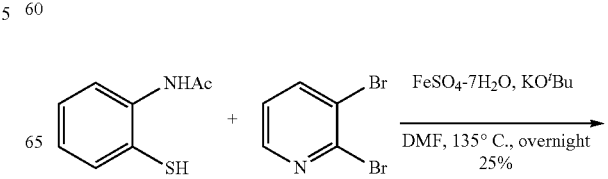

Synthesis of 3
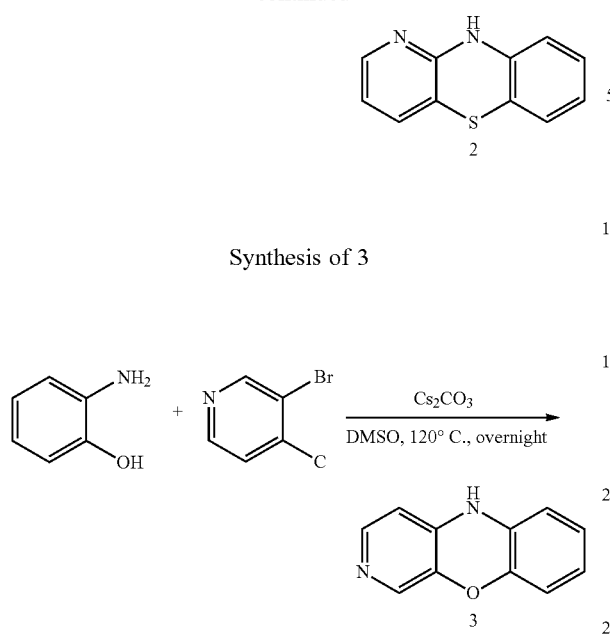
Synthesis of 4
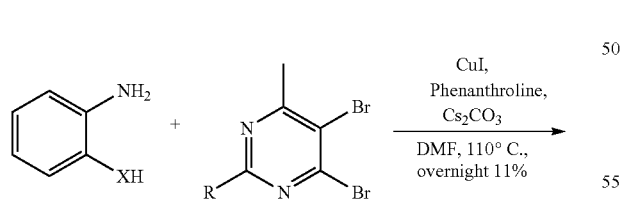
Synthesis of 5 and 6
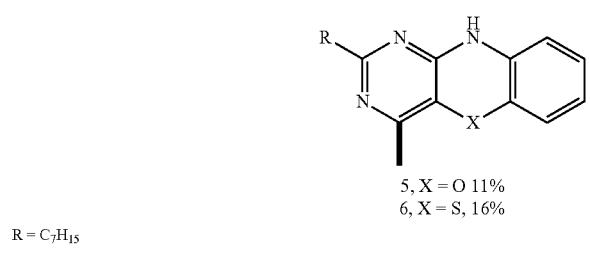
R = C₇H₁₅
Synthesis of 7 and 8
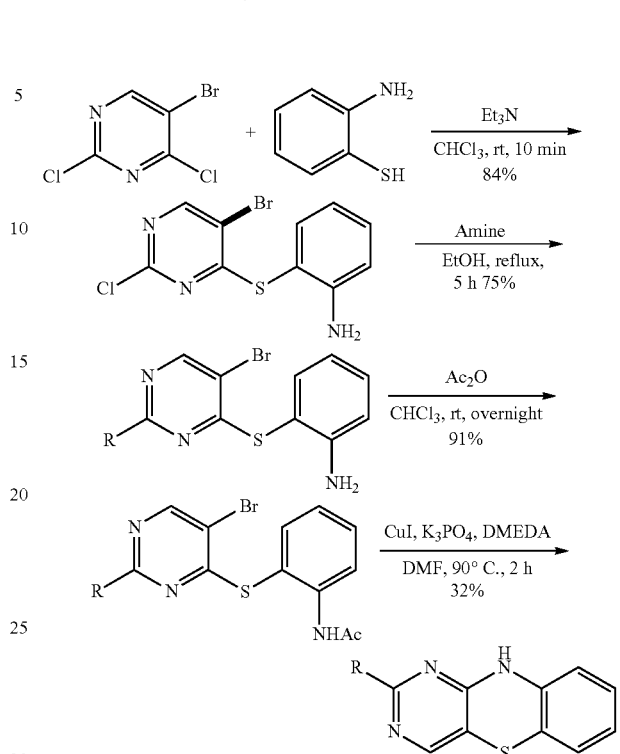
R = Pyrrolidine, Et₂N
Synthesis of 9
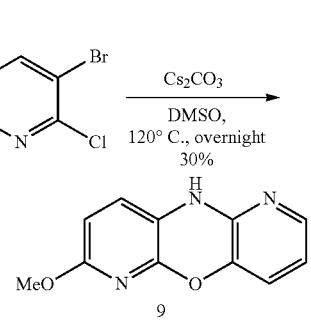
Synthesis of 10
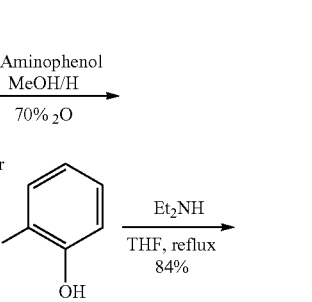

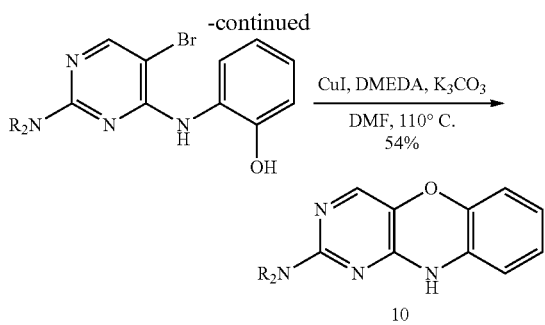

TABLE 1

Inhibition Rate Constants and Stoichiometries of 1-9

| Compound | $k_{inh}$ (M$^{-1}$s$^{-1}$) | n |
|---|---|---|
| 1 | (6.8 ± 0.2) × 10$^5$ | 50 ± 1 |
| 2 | (2.8 ± 0.1) × 10$^5$ | 10 ± 2 |
| 3 | (1.3 ± 0.2) × 10$^5$ | 183 ± 8 |
| 4 | (5.9 ± 0.5) × 10$^5$ | 46 ± 3 |
| 5 | (9.0 ± 0.3) × 10$^5$ | 109 ± 4 |
| 6 | (3.3 ± 0.2) × 10$^5$ | —[a] |
| 7 | (2.0 ± 0.1) × 10$^5$ | 4 ± 0.4 |
| 8 | (2.6 ± 0.1) × 10$^5$ | 6 ± 0.1 |
| 9 | (5.6 ± 0.3) × 10$^5$ | 15 ± 2 |
| 10 | (2.4 ± 0.4) × 10$^6$ | 11 ± 0.7 |

Table 1. Inhibition rate constants, $k_{inh}$, and stoichiometries, n, for compounds 1-9, measured in hexadecane/PBD-BODIPY co-autoxidations at 70° C. in PhCl. [a] Inefficient turnover. Relative to other antioxidants, autoxidation was inhibited poorly in the catalytic phase. Dye consumption prevented accurate determination of the stoichiometry.

Characterization Data

1-Azaphenoxazine (1):
$^1$H-NMR (500 MHz; DMSO-d6): δ9.01 (s, 1H), 7.53 (dd, J=5.0, 1.4 Hz, 1H), 6.90-6.88 (m, 1H), 6.76 (ddd, J=7.7, 6.9, 2.0 Hz, 1H), 6.65-6.61 (m, 2H), 6.59-6.54 (m, 2H). 13-C NMR (126 MHz; DMSO): δ146.4, 142.7, 142.1, 139.5, 131.8, 124.6, 121.7, 121.0, 117.0, 115.5, 114.5 HRMS (EI): Calc'd for $C_{11}H_8N_2O$: 184.0637, Found: 184.0652

1-Azaphenothiazine (2):
$^1$H-NMR (300 MHz; C6H6): δ9.20 (s, $^1$H), 7.81 (dd, J=4.9, 1.6 Hz, 1H), 7.27 (ddd, J=7.5, 1.6, 0.5 Hz, 1H), 7.00 (ddd, J=8.0, 7.2, 1.5 Hz, 1H), 6.92 (dd, J=7.7, 1.5 Hz, $^1$H), 6.84-6.76 (m, 2H), 6.73 (dd, J=7.5, 4.9 Hz, $^1$H). 13-C NMR (76 MHz; DMSO): δ153.0, 145.5, 140.7, 133.7, 127.6, 125.8, 122.4, 117.8, 115.17, 115.06, 112.0 HRMS (EI): Calc'd for $C_{11}H_8N_2S$: 200.0408, Found: 200.0400

3-Azaphenoxazine (3):
$^1$H-NMR (400 MHz; DMSO-d6): δ8.80 (s, 1H), 7.78 (d, J=5.1 Hz, 1H), 7.69 (s, 1H), 6.79-6.75 (m, 1H), 6.66-6.64 (m, 2H), 6.50 (dt, J=7.4, 0.7 Hz, 1H), 6.39 (d, J=5.1 Hz, 1H). 13-C NMR (151 MHz; DMSO): δ146.6, 143.5, 140.7, 139.4, 135.7, 130.9, 124.7, 122.3, 116.0, 114.6, 108.2 HRMS (EI): Calc'd for $C_{11}H_8N_2O$: 184.0637, Found: 184.0646

3-Azaphenothiazine (4):
$^1$H-NMR (400 MHz; DMSO-d6): δ9.10 (s, 1H), 7.98 (d, J=5.4 Hz, 1H), 7.88 (s, 1H), 7.02 (td, J=7.6, 1.3 Hz, 1H), 6.94 (dd, J=7.7, 1.2 Hz, 1H), 6.81 (td, J=7.5, 1.2 Hz, 1H), 6.68 (dd, J=7.9, 1.1 Hz, 1H), 6.55 (d, J=5.4 Hz, 1H). 13-C NMR (151 MHz; DMSO): δ149.2, 148.5, 146.1, 140.2, 128.3, 127.2, 123.5, 116.2, 115.6, 113.6, 109.2, 40.0 HRMS (EI): Calc'd for $C_{11}H_8N_2S$: 200.0408, Found: 200.0415

2-Heptyl-4-methyl-1,3-Diazaphenoxazine (5): $^1$H-NMR (400 MHz; DMSO-d6): δ9.52 (s, 1H), 6.78 (ddd, J=7.7, 5.5, 3.3 Hz, 1H), 6.72-6.69 (m, 2H), 6.59 (d, J=7.1 Hz, 1H), 2.45 (t, J=7.7 Hz, 2H), 2.10 (s, 3H), 1.61 (dd, J=7.9, 7.1 Hz, 2H), 1.27-1.25 (m, 8H), 0.86 (t, J=6.9 Hz, 3H). 13-C NMR (151 MHz; DMSO): δ164.2, 150.9, 147.4, 143.7, 133.7, 130.3, 124.6, 123.0, 115.9, 115.3, 38.2, 31.7, 29.16, 29.01, 28.4, 22.6, 17.4, 14.4 HRMS (EI): Calc'd for $C_{18}H_{23}N_3O$: 297.1841, Found: 297.1829

2-Heptyl-4-methyl-1,3-Diazaphenothiazine (6):
$^1$H-NMR (400 MHz; DMSO-d6): δ9.60 (s, 1H), 7.01-6.93 (m, 2H), 6.82-6.77 (m, 2H), 2.49 (d, J=9.5 Hz, 2H), 1.65-1.61 (m, 2H), 1.26 (t, J=5.3 Hz, 8H), 0.87-0.84 (m, 3H). 13-C NMR (151 MHz; DMSO): δ167.6, 158.9, 157.9, 139.1, 128.2, 126.6, 123.8, 116.40, 116.27, 105.6, 38.3, 31.6, 29.2, 29.0, 28.3, 22.5, 21.6, 14.4 HRMS (EI): Calc'd for $C_{18}H_{23}N_3S$: 313.1613, Found: 297.1635

2-Diethylamino-1,3-Diazaphenothiazine (7):
$^1$H-NMR (500 MHz; DMSO-d6): δ9.39 (s, 1H), 7.63 (s, 1H), 7.02-6.98 (m, 1H), 6.93 (dd, J=20.3, 7.8 Hz, 2H), 6.84-6.80 (m, 1H), 3.50 (q, J=7.0 Hz, 4H), 1.09 (t, J=7.0 Hz, 6H). 13-C NMR (126 MHz; DMSO): δ159.9, 158.9, 152.2, 139.6, 127.7, 126.5, 123.5, 117.2, 116.4, 95.2, 41.5, 13.7 HRMS (EI): Calc'd for $C_{14}H_6N_4S$: 272.1096, Found: 272.1084

2-(Pyrrolidn-1-yl)-1,3-Diazaphenothiazine (8):
$^1$H-NMR (400 MHz; DMSO-d6): δ9.45 (s, 1H), 7.63 (s, 1H), 7.02-6.97 (m, 1H), 6.92 (m, J=1.2 Hz, 2H), 6.82 (td, J=7.5, 1.2 Hz, 1H), 3.41 (m, 4H), 1.90-1.86 (m, 4H). 13-C NMR (76 MHz; DMSO): δ159.4, 158.9, 152.1, 139.5, 127.7, 126.5, 123.6, 117.2, 116.4, 95.4, 46.8, 25.4 HRMS (EI): Calc'd for $C_{14}H_{14}N_4S$: 272.0939, Found: 272.0948

3-Methoxy-4,9-Diazaphenothiazine (9):
$^1$H-NMR (500 MHz; DMSO-d6): δ8.97 (s, 1H), 7.77 (dd, J=4.9, 1.6 Hz, 1H), 7.25 (dd, J=7.5, 1.5 Hz, 1H), 7.07 (d, J=8.6 Hz, 1H), 6.69 (dd, J=7.5, 4.9 Hz, 1H), 6.47 (d, J=8.6 Hz, 1H), 3.71 (s, 3H). 13-C NMR (126 MHz; DMSO): δ159.2, 152.8, 146.3, 134.8, 134.6, 131.5, 126.2, 117.9, 112.4, 108.8, 53.9 HRMS (EI): Calc'd for $C_{11}H_9N_3OS$: 231.0466, Found: 231.0460

2-Diethylamino-1,3-Diazaphenothiazine (10):
$^1$H-NMR (400 MHz; DMSO-d$_6$): δ9.39 (s, 1H), 7.46 (d, J=0.7 Hz, 1H), 6.77 (td, J=7.4, 1.7 Hz, 1H), 6.72-6.65 (m, 3H), 3.45 (q, J=7.0 Hz, 4H), 1.07 (t, J=7.0 Hz, 6H). 13-C NMR (151 MHz; DMSO): δ156.8, 151.1, 143.2, 139.1, 129.46, 129.26, 123.4, 122.3, 115.09, 114.89, 41.2, 13.3 HRMS (EI): Calc'd $C_{14}H_{16}N_4O$: 256.1324, Found: 256.1354.

References (1) Shen, C.; Wu, X.-F. Catal. Sci. Technol. 2015, 5, 4433-4443.

(2) Hu, W.; Zhang, S. J. Org. Chem. 2015, 80, 6128-6132.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are indicative of the level of skill those skilled in the art to which this invention pertains and are herein incorporated by reference to the same extent as if

What is claimed is:

1. A lubricant composition useful for engines, comprising:
an oil of lubricating viscosity, and
a compound selected from the group consisting of:
a compound of Formula (I):

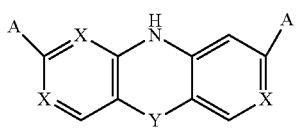

wherein:
X is CH or N, wherein at least one X is N, and wherein:
(i) Y is O, and A is either H or an electron donating group; wherein said electron donating group is an H atom, a hydrocarbon group, an aryl group, an alkyl group, an alkoxy group, an amine group, a monosubstituted amine, or a disubstituted amine, or
(ii) Y is S and A is either H or an electron donating group, wherein at least one A is an electron donating group when the ring to which it is attached comprises at least one X that is N; and wherein said electron donating group is a hydrocarbon group, an aryl group, an alkyl group, an alkoxy group, an amine group, a monosubstituted amine, or a disubstituted amine;

a compound of Formula (II)

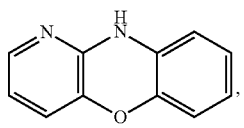

a compound of Formula (IV)

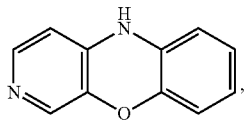

a compound of Formula (VI):

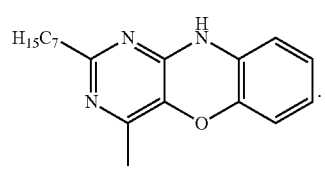

a compound of Formula (VII):

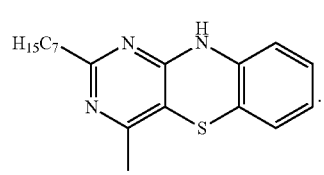

a compound of Formula (VIII):

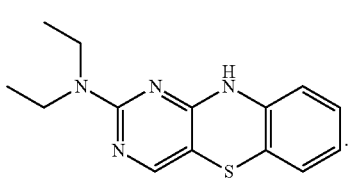

a compound of Formula (IX):

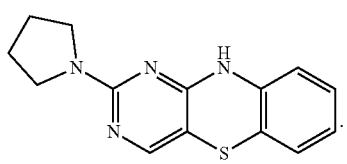

a compound of Formula (X):

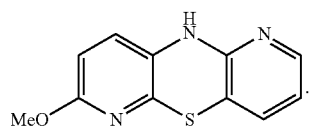

and
a compound of Formula (XI):

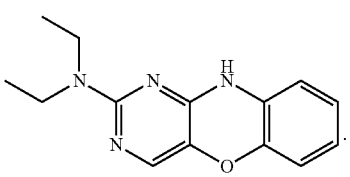

2. The lubricant composition of claim 1, wherein said oil of lubricating viscosity comprises a natural oil, a synthetic oil, or a mixture of a natural oil and a synthetic oil.

3. The lubricant composition of claim 1, where said oil of lubricating viscosity comprises an API base oil of Group I, Group II, Group III, Group IV, or Group V.

4. The lubricant composition of claim 1, further comprising an additive.

5. The lubricant composition of claim 4, wherein said additive comprises one or more of a metal deactivator, a detergent, a friction modifier, an antiwear agent, a rust inhibitor, a dispersant, a viscosity index improver, an extreme pressure agent, an additional antioxidant, a foam inhibitor, a pour point depressant, and a seal swelling agent.

6. A method of forming a lubricant composition useful for engines, comprising combining an oil of lubricating viscosity with a compound selected from the group consisting of:

a compound of Formula (I):

(I)

wherein:

X is CH or N, wherein at least one X is N, and wherein:
(i) Y is O, and A is either H or an electron donating group; wherein said electron donating group is an H atom, a hydrocarbon group, an aryl group, an alkyl group, an alkoxy group, an amine group, a monosubstituted amine, or a disubstituted amine, or
(ii) Y is S and A is either H or an electron donating group, wherein at least one A is an electron donating group when the ring to which it is attached comprises at least one X that is N; and wherein said electron donating group is a hydrocarbon group, an aryl group, an alkyl group, an alkoxy group, an amine group, a monosubstituted amine, or a disubstituted amine;

a compound of Formula (II)

(II)

a compound of Formula (IV)

(IV)

a compound of Formula (VI):

(VI)

a compound of Formula (VII):

(VII)

a compound of Formula (VIII):

(VIII)

a compound of Formula (IX):

(IX)

a compound of Formula (X):

(X)

and
a compound of Formula (XI):

(XI)

7. The method of claim 6, wherein said oil of lubricating viscosity comprises a natural oil, a synthetic oil, or a mixture of a natural oil and a synthetic oil.

8. The method of claim 7, where said oil of lubricating viscosity comprises an API base oil of Group I, Group II, Group III, Group IV, or Group V.

9. The method of claim 6, further comprising combining an additive.

10. The method of claim 9, wherein said additive comprises one or more of a metal deactivator, a detergent, a friction modifier, an antiwear agent, a rust inhibitor, a dispersant, a viscosity index improver, an extreme pressure agent, an additional antioxidant, a foam inhibitors, a pour point depressant, and a seal swelling agent.

11. A kit comprising the lubricant composition of claim 1.

12. The kit of claim 11, wherein said oil of lubricating viscosity comprises a natural oil, a synthetic oil, or a mixture of a natural oil and a synthetic oil.

13. The kit of claim 12, where said oil of lubricating viscosity comprises an API base oil of Group I, Group II, Group III, Group IV, or Group V.

14. The kit of claim 11, wherein the lubricant composition further comprises an additive.

15. The kit of claim 14, wherein said additive comprises one or more of a metal deactivator, a viscosity modifier, a detergent, a friction modifier, an antiwear agent, a rust inhibitor, a corrosion inhibitor, a dispersant, a dispersant viscosity modifier, a viscosity index improver, an extreme pressure agent, an additional antioxidant, and a foam inhibitor.

16. A method of lubricating a combustion engine comprising applying a lubricant composition comprising an oil of lubricating viscosity and a compound selected from the group consisting of:

a compound of Formula (I):

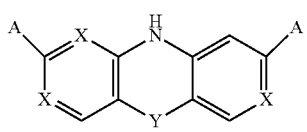

wherein:

X is CH or N, wherein at least one X is N, and wherein:

(i) Y is O, and A is either H or an electron donating group; wherein said electron donating group is an H atom, a hydrocarbon group, an aryl group, an alkyl group, an alkoxy group, an amine group, a monosubstituted amine, or a disubstituted amine, or (ii) Y is S and A is either H or an electron donating group, wherein at least one A is an electron donating group when the ring to which it is attached comprises at least one X that is N; and wherein said electron donating group is a hydrocarbon group, an aryl group, an alkyl group, an alkoxy group, an amine group, a monosubstituted amine, or a disubstituted amine;

a compound of Formula (II)

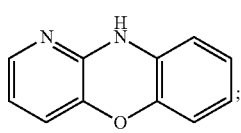

a compound of Formula (IV)

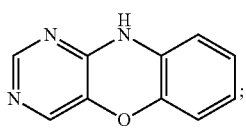

a compound of Formula (VI):

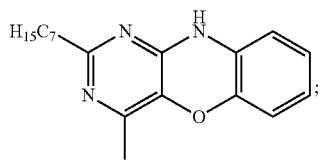

a compound of Formula (VII):

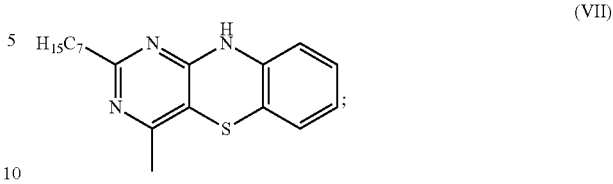

a compound of Formula (VIII):

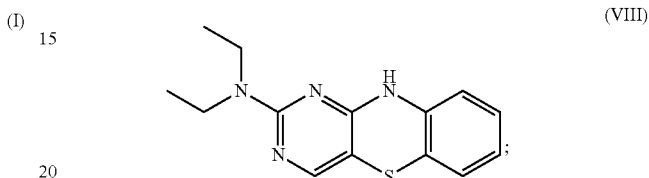

a compound of Formula (IX):

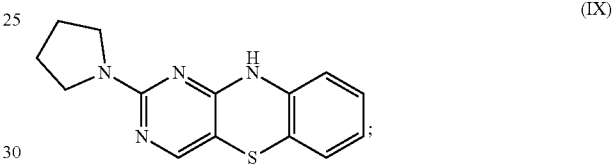

a compound of Formula (X):

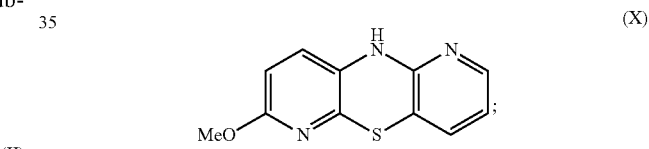

and
a compound of Formula (XI):

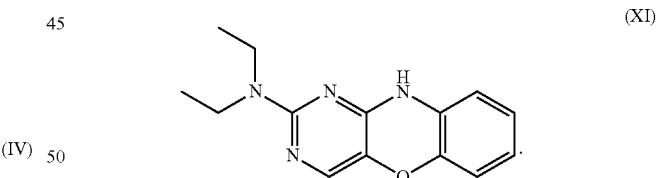

17. The method of claim 16, wherein said oil of lubricating viscosity comprises a natural oil, a synthetic oil, or a mixture of a natural oil and a synthetic oil.

18. The method of claim 16, wherein the lubricant composition further comprises an additive.

19. The lubricant composition of claim 1, wherein the composition is useful for engine operating temperatures of at least 100° C.; or at least 160° C.

20. The method of claim 6, wherein the lubricant composition is useful for engine operating temperatures of at least 100° C. or at least 160° C.

21. The method of claim 16, wherein the lubricant composition is useful for engine operating temperatures of at least 100° C. or at least 160° C.

* * * * *

UNITED STATES PATENT AND TRADEMARK OFFICE
CERTIFICATE OF CORRECTION

PATENT NO. : 11,512,262 B2  
APPLICATION NO. : 16/494936  
DATED : November 29, 2022  
INVENTOR(S) : Derek Andrew Pratt et al.

Page 1 of 1

It is certified that error appears in the above-identified patent and that said Letters Patent is hereby corrected as shown below:

In the Claims

Column 24, Line 57, replace "where said" with --wherein said--.

Column 26, Line 45, replace "where said" with --wherein said--;
    Line 55, replace "inhibitors" with --inhibitor--.

Column 27, Line 50, replace " 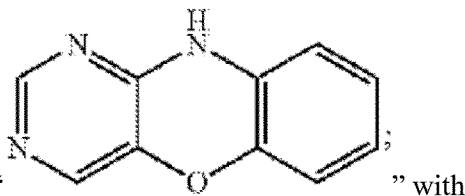 " with 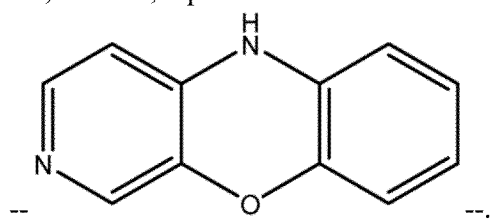 --.

Signed and Sealed this
Eleventh Day of April, 2023

Katherine Kelly Vidal
*Director of the United States Patent and Trademark Office*